US007279319B2

(12) United States Patent
Cheng

(10) Patent No.: US 7,279,319 B2
(45) Date of Patent: Oct. 9, 2007

(54) METHOD AND APPARATUS FOR INJECTING OXYGEN INTO FERMENTATION PROCESSES

(75) Inventor: Alan Tat-Yan Cheng, Livingston, NJ (US)

(73) Assignee: Praxair Technology, Inc., Danbury, CT (US)

( * ) Notice: Subject to any disclaimer, the term of this patent is extended or adjusted under 35 U.S.C. 154(b) by 400 days.

(21) Appl. No.: 10/985,913

(22) Filed: Nov. 12, 2004

(65) Prior Publication Data

US 2005/0067724 A1 Mar. 31, 2005

Related U.S. Application Data

(62) Division of application No. 09/985,001, filed on Nov. 1, 2001, now Pat. No. 7,048,262.

(51) Int. Cl.
*C12N 1/00* (2006.01)
*B01D 47/02* (2006.01)

(52) U.S. Cl. .................................... 435/243; 261/121.1

(58) Field of Classification Search ................ 435/243; 261/121.1

See application file for complete search history.

(56) References Cited

U.S. PATENT DOCUMENTS 136,208 A * 2/1873 Bond
396,507 A * 1/1889 Pearson
404,621 A * 6/1889 Hibbert
661,276 A * 11/1900 Reenstrierna
706,600 A * 8/1902 Rush
712,368 A * 10/1902 Ebner
742,533 A * 10/1903 Walther
1,673,188 A * 6/1928 Eggert
2,402,132 A * 6/1946 Goldberg
2,868,523 A * 1/1959 Cundiff et al.
3,081,289 A * 3/1963 Cheney et al.
3,997,300 A * 12/1976 Boatwright et al.
4,044,079 A * 8/1977 Tveit
4,182,617 A * 1/1980 Al-Saidi
4,302,406 A * 11/1981 van Heel
4,407,718 A * 10/1983 Pollock ..................... 210/626
4,446,081 A * 5/1984 Arinobu
4,722,785 A * 2/1988 Reid
5,356,600 A 10/1994 Kiyonaga et al. ........... 422/234
5,798,254 A * 8/1998 Cheng ........................ 435/234
5,928,615 A * 7/1999 Strock et al.
5,939,313 A 8/1999 Cheng ..................... 435/289.1
5,985,652 A 11/1999 Cheng ..................... 435/289.1
5,994,567 A 11/1999 Kingsley et al. ............ 552/208
6,561,498 B2 * 5/2003 Tompkins et al.
7,048,262 B2 * 5/2006 Cheng ..................... 261/121.1

FOREIGN PATENT DOCUMENTS

DE 3447060 A1 * 7/1986

* cited by examiner

*Primary Examiner*—Jon Weber
*Assistant Examiner*—Kailash C. Srivastava
(74) *Attorney, Agent, or Firm*—Robert J. Hampsch

(57) ABSTRACT

A sparger for delivering fluid comprising a sparger pipe for carrying the fluid from a fluid source and downwardly directed nozzles to direct the delivery of fluid is disclosed. A substantially vertical connection pipe connects the sparger to the nozzles. Also, a method of delivering oxygen to an oxygen-depleted zone in the bottom of the fermenter using the sparger is disclosed.

8 Claims, 3 Drawing Sheets

METHOD AND APPARATUS FOR INJECTING OXYGEN INTO FERMENTATION PROCESSES

CROSS REFERENCE TO RELATED APPLICATIONS

This a Division of prior U.S. application Ser. No. 09/985,001. Filing Date: Nov. 1, 2001 now U.S. Pat. No. 7,048,262.

FIELD OF THE INVENTION

This invention is related to a device for delivering fluids and a method for using the device. More specifically, this invention is related to a sparger for delivering oxygen to a fermentation broth, and a method for its use.

BACKGROUND OF THE INVENTION

Oxygen is one of the essential nutrients that bacteria or fungus requires in an aerobic fermentation process. The oxygen is usually provided by sparging air through a sparge ring in a submerged culture fermentation broth. The sparge ring is often a round metal ring with tens or hundreds of holes drilled on it.

A fermentation broth contains not only biomass, but also carbohydrate such as molasses, corn starch, sugar or corn syrup. Some formulations may also contain vegetable oil as a source of energy and a whole range of minerals and nutrients necessary to keep the biomass healthy.

However, a dense biomass together with the food/nutrients may make the resulting fermentation broth very viscous, which in turn tends to reduce the efficiency of dissolution and transfer of the sparged oxygen to the broth. There is also a potential hazard of having the fermentation broth backing up into the sparger and plugging up some of the holes. Sparger plugging presents a major problem because plugged holes reduce the gas dispersion efficiency. Additionally, the biomass entering the sparger will grow and mutate, resulting in eventual contamination of the fermentation broth.

SUMMARY OF THE INVENTION

This invention is directed to a sparger for delivering fluid comprising a sparger pipe for carrying the fluid from a fluid source and downwardly directed nozzles to direct the delivery of fluid. The downwardly directed nozzles are also drainage holes to drain fluids. A substantially vertical connection pipe linking the sparger to the injector nozzles is preferably used. A flow restrictor comprised of sintered metal plates or calibrated orifices is placed on the connection pipe to regulate the flow of fluid delivery through each of the nozzles.

The sparger pipe may be a straight substantially-horizontal pipe. A plurality of nozzles are directed away from one another and positioned at about 45 degrees to substantially vertical. The sparger generates fluid bubbles.

In another embodiment, this invention is directed to a method for delivering fluid to a fermentation vessel having an oxygen-depleted zone in the vessel and comprising both air spargers and oxygen spargers therein, the method comprises injecting air bubbles through the air spargers at the outer end of the vessel, and injecting oxygen bubbles downwardly through the oxygen spargers at the center of the vessel. The oxygen bubbles are injected at a downward direction through the oxygen sparger to an area between the air sparger.

In yet another embodiment, this invention is directed to a fermentation vessel having an oxygen-depleted zone within the fermentation broth and comprising a plurality of air spargers and oxygen spargers therein, with at least one air sparger located next to at least one oxygen sparger, the method comprises injecting air bubbles through the air spargers at one position at the bottom of the vessel, and injecting oxygen bubbles downwardly through the oxygen spargers adjacent to the air sparger.

As used herein, the term fermentation “vessel” is also applicable, and may refer, to a fermentation “reactor”.

BRIEF DESCRIPTION OF THE DRAWINGS

The invention is hereinafter described with reference to the accompanying drawings in which.

DETAILED DESCRIPTION OF THE INVENTION

Figure 1:
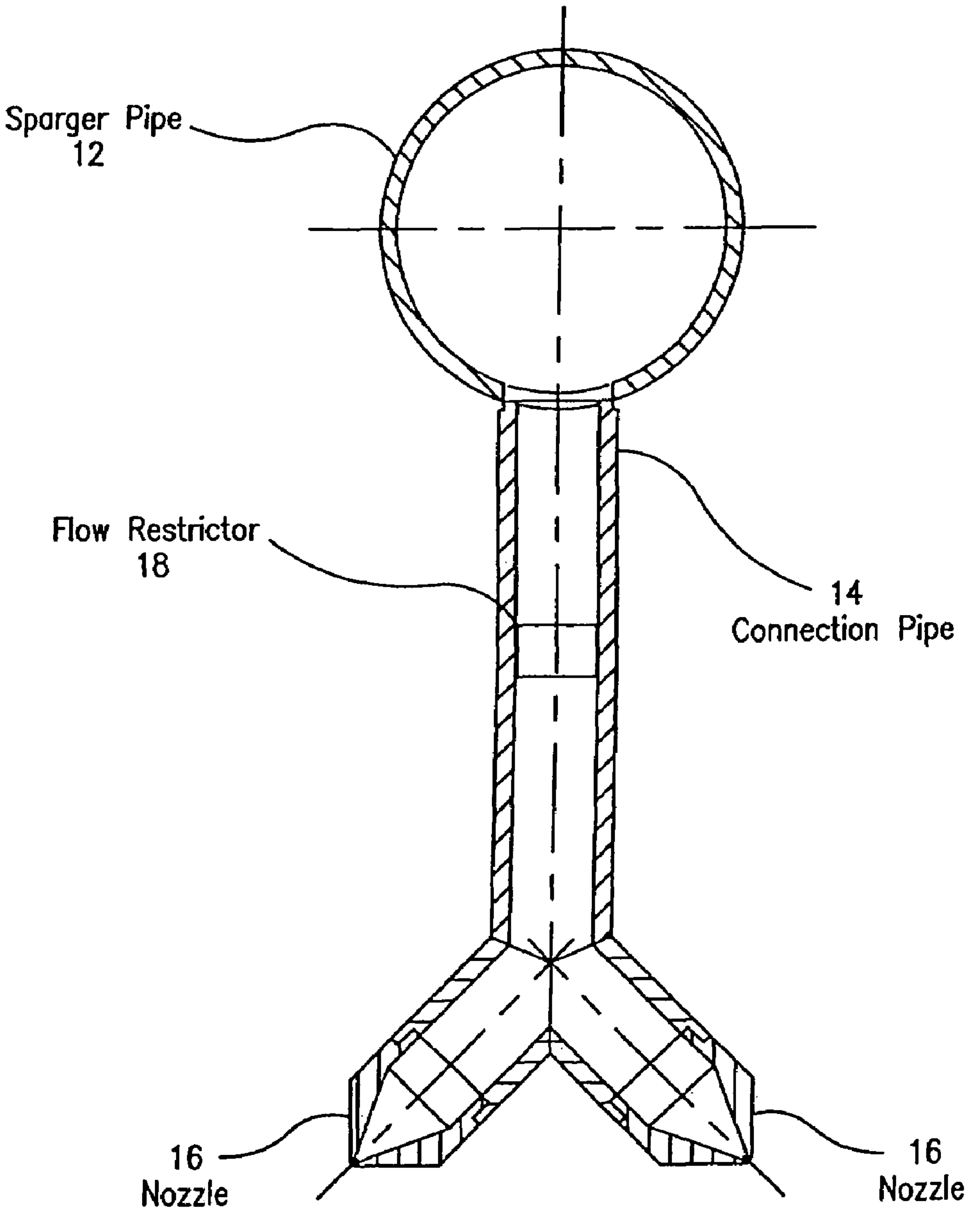
FIG. 1 is a side view of the sparger assembly of this invention.

Generally, air has traditionally been used as the sole means of providing oxygen to the fermentation process. The problem with biomass entering the air sparger is small. This is due to high air flow rates required by fermentation systems. At these high air flow rates, the air velocity through the sparger holes is also high, and back-flow of fermentation broth into the sparger is not possible.

Sparger design also plays a role in the size of the air bubbles injected into the fermenter. Smaller holes generally create smaller bubbles. However, there is a practical limitation on how small such holes can be manufactured. Furthermore, bubble formation is a complex physical process that depends on many factors, including the inertia of the injected gas and the viscosity and interfacial tension of the fermentation broth. In viscous fermentation systems, gas inertia is often insufficient to overcome broth viscosity and interfacial tension effects. Consequently, the bubbles form and detach from the sparger are significantly larger than the size of the sparger holes. These large gas bubbles can even coalesce with the gas bubbles from neighboring holes to form larger bubble before detaching from the sparger. Therefore, it is not beneficial to have a large number of very small holes, as the gas will tend to coalesce to form significantly larger size bubbles. This is one reason why a porous sintered metal sparger is not regarded as particularly useful in this application.

There is another factor that indicates the use of larger holes in the air sparger. Fermentations are in general batch processes, which require air only during a portion of the cycle. Some biomass will tend to enter the sparger during a part of the cycle when the gas is not required. Therefore, these sparger holes are generally enlarged to 4 mm or bigger so that suspended solids entering the sparger can still be washed out with steam. Several larger drain holes are drilled in the bottom of the sparger so that the condensate can be washed out.

However, it is possible to inject pure oxygen directly into the fermenter, separately from the air sparger. This direct oxygen injection process is advantageous because it provides better oxygen mass transfer efficiency than is obtained by pre-mixing the air with the same volumetric flow of oxygen prior to injection. Design of direct oxygen injection systems creates a new challenge because pure oxygen injection requires significantly less gas flow than air injection. To supply the same amount of contained oxygen to a fermenter, the volumetric flow rate of a pure oxygen stream will be approximately ⅕ of that obtained with air. Therefore, oxygen sparger design will be different from that of an air sparger. Backflow of the fermentation broth has additional risks with pure oxygen. If the broth material enters the sparger and dries up, the dried organic material in the presence of pure oxygen creates an environment that may support combustion. Certain types of biological material entering the sparger may also grow faster in an oxygen rich environment. Because of the buoyancy force of the gas bubbles, it is undesirable to locate the sparger holes in the bottom of the sparger. Any gas bubbles exiting from the holes will try to rise by hitting the sparger surface. A portion of gas bubbles will adhere to the sparger surface and coalesce into larger gas bubbles. Therefore, generally only larger draining holes are located in the bottom of the sparger.

The draining holes are generally made bigger than the sparger holes to reduce the chance of plugging. However, the air or oxygen will travel towards the path of least resistance by passing a major portion through the draining hole. The gas bubbles from the draining holes will be bigger as it escapes from the draining holes, which are bigger than the sparger holes. It also has the undesirable effect of hitting the sparger pipe when rising due to the buoyancy. Therefore, it is general practice to limit the number of draining holes to about 4. When the sparge ring is not constructed and installed perfectly, some liquid will collect at unintentional low points, away from the drain holes. Furthermore, any blockage at one of the drainage hole will create a significant amount of aqueous biomass retained inside the sparger. Any dissolved or suspended particulate left after the steam sterilization cycle may pose a processing problem as the oxygen will dry up the solution, leaving behind a solid film, which may ultimately build up to a thick layer.

It is for the above reasons why it is desirable to develop a new type of oxygen injection sparger that meets the new demand of this oxygen application.

In this invention, downward injection nozzles are used in place of conventional sparger holes. This provides more accurate control of the gas velocity, even at reduced gas flow rate. The nozzles provide a compression cone arrangement allowing gas to be accelerated towards the end of the nozzle at the exit point.

As shown in FIG. 1, every single nozzle also serves as a draining hole. There are no differences between the size of the gas injection nozzle and the draining hole. Therefore, a sparger with 200 nozzles will have 200 draining holes. Gas flow will be evenly distributed across the nozzles and the resultant gas dispersion in the broth will also be distributed uniformly across the nozzles.

The downward injection allows the oxygen gas injected to oxygenate a volume of liquid located below the sparger. This is usually ignored in an agitated tank since air spargers are designed to feed the impeller directly. This is a critical issue in air-lifted fermenters. In air-lifted fermenters, the bottom of the vessel is not directly agitated. Only convective liquid movement downward to offset the upflow driven by gas buoyancy provides mixing at the bottom of the fermenter. Additionally, this part of the liquid often has the lowest concentration of oxygen, resulting in oxygen “starved” conditions at the bottom of the air-lifted fermenter. Conventional air spargers have holes located on the side and top of the sparger, and are not able to provide oxygen to that section of the vessel.

Using the oxygen nozzles as shown in this invention has another advantage. The nozzle will force the oxygen through the compression cone, increasing the exit velocity. The higher velocity allows additional agitation and entrainment of the liquid in the bottom of the vessel. Bubbles from conventional sparger holes will move upwards immediately, as the buoyancy force will overcome the weak injection force.

Even with downward injection nozzles, the rising gas bubbles formed will not hit the bottom of the sparger pipe due to the unique design of the split nozzles that gas bubbles formed will escape around the sparger pipe.

FIG. 1 shows the details of the downward injecting oxygen sparger design. The top is the cross-sectional area of sparger pipe 12. Sparger pipe 12 is usually a ring shape with circular cross-section for agitated tank but it can be straight horizontal pipes also for air-lifted fermenters. Note that straight connect pipe 14 allows any liquid drain off from the sparger pipe.

The bottom of the connecting pipe is split into two nozzles 16, pointing the opposite directions and about 45 degree to vertical. This allows a stream of gas bubbles to form at the nozzles and rise unrestricted. Note that the vertical entrain point is wider than the diameter of the sparger pipe. A connection pipe connects the sparger pipe to the nozzles.

Note that this downward sparging system has no low points inside the entire system. The only low point is at the exit of the nozzle. This allows the entire oxygen sparging system to be steam sterilized. Any condensate will be dripped off the sparger. It also allows the sparger to be washed with caustic solution or water for cleaning between batches.

This invention also provides for methods to deliver oxygen into the fermentation vessel. The oxygen sparger delivering pure (or substantially pure) oxygen can be positioned at various location in the fermentation vessel.

Figure 2:
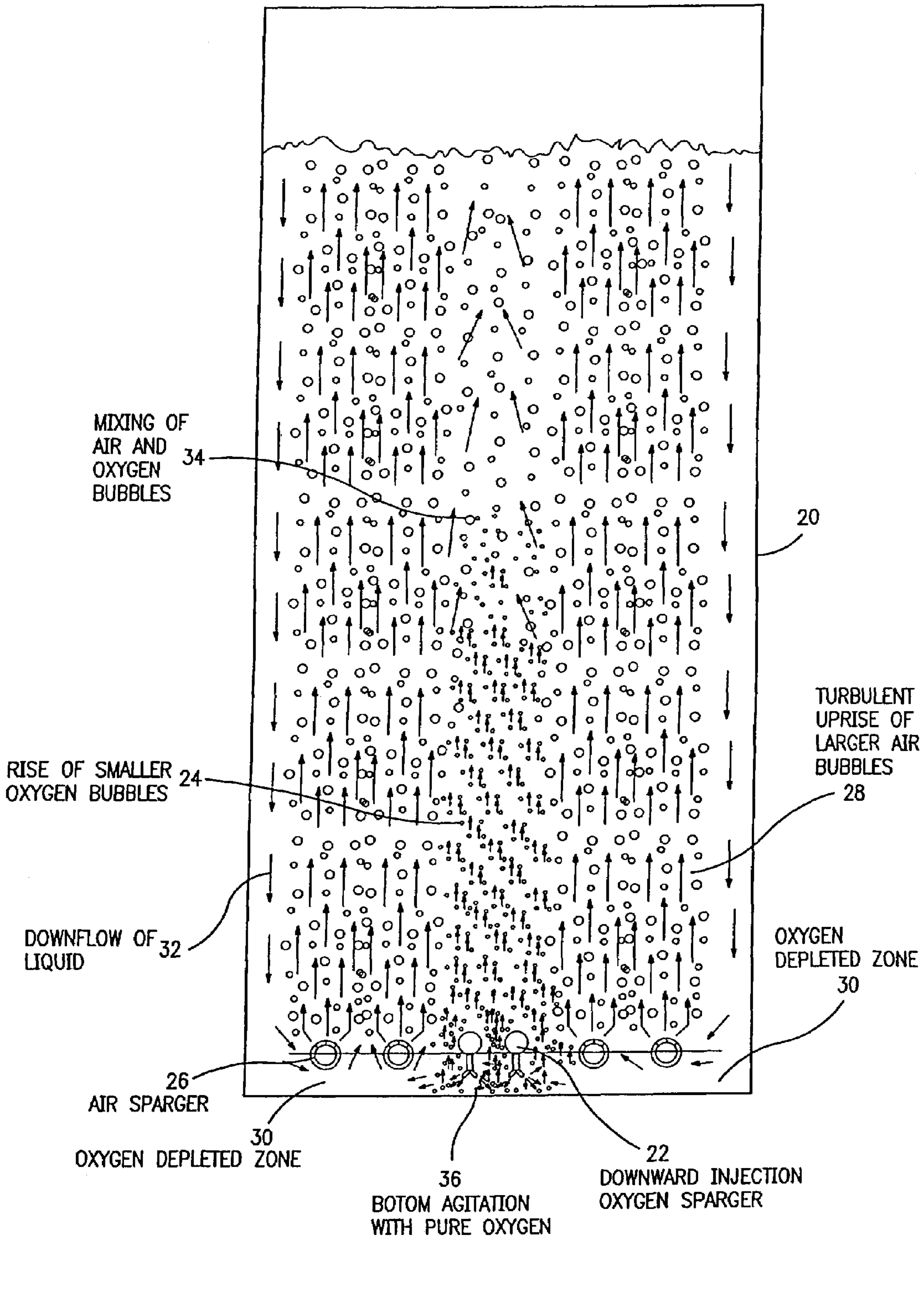
FIG. 2 is a side of a fermentation vessel showing the center position of the oxygen spargers relative to the outer position of the air spargers therein in this invention.

FIG. 2 shows fermentation vessel 20 having the center position of oxygen spargers 22 relative to the outer position of air spargers 26 therein in this invention. Downward injection oxygen spargers 22 direct the oxygen toward and into an oxygen-depleted zone 30 causing bottom agitation 36 with pure oxygen from the oxygen sparger 22. Small oxygen bubbles 24 from oxygen sparger 22 float upward in fermentation vessel 20. Air sparger 26 passes larger size bubbles 28, which rise turbulently upward. Liquid 32 flows downward on the side of the fermentation vessel 20 towards the edge of the vessel walls and at the bottom proximate to the oxygen depleted zone 30. It should be recognized that this discussion of hydrodynamics is a gross simplication. In a time averaged sense the liquid flow at the fermenter wall is downward, but the instantaneous liquid flow near the wall can be oriented in any direction. The flows are highly chaotic and complex and the representations in the text and figures are for illustrative purposes. The small oxygen bubbles 24 and large air bubbles 28 are mixed in fermentation vessel area 34.

Figure 3:
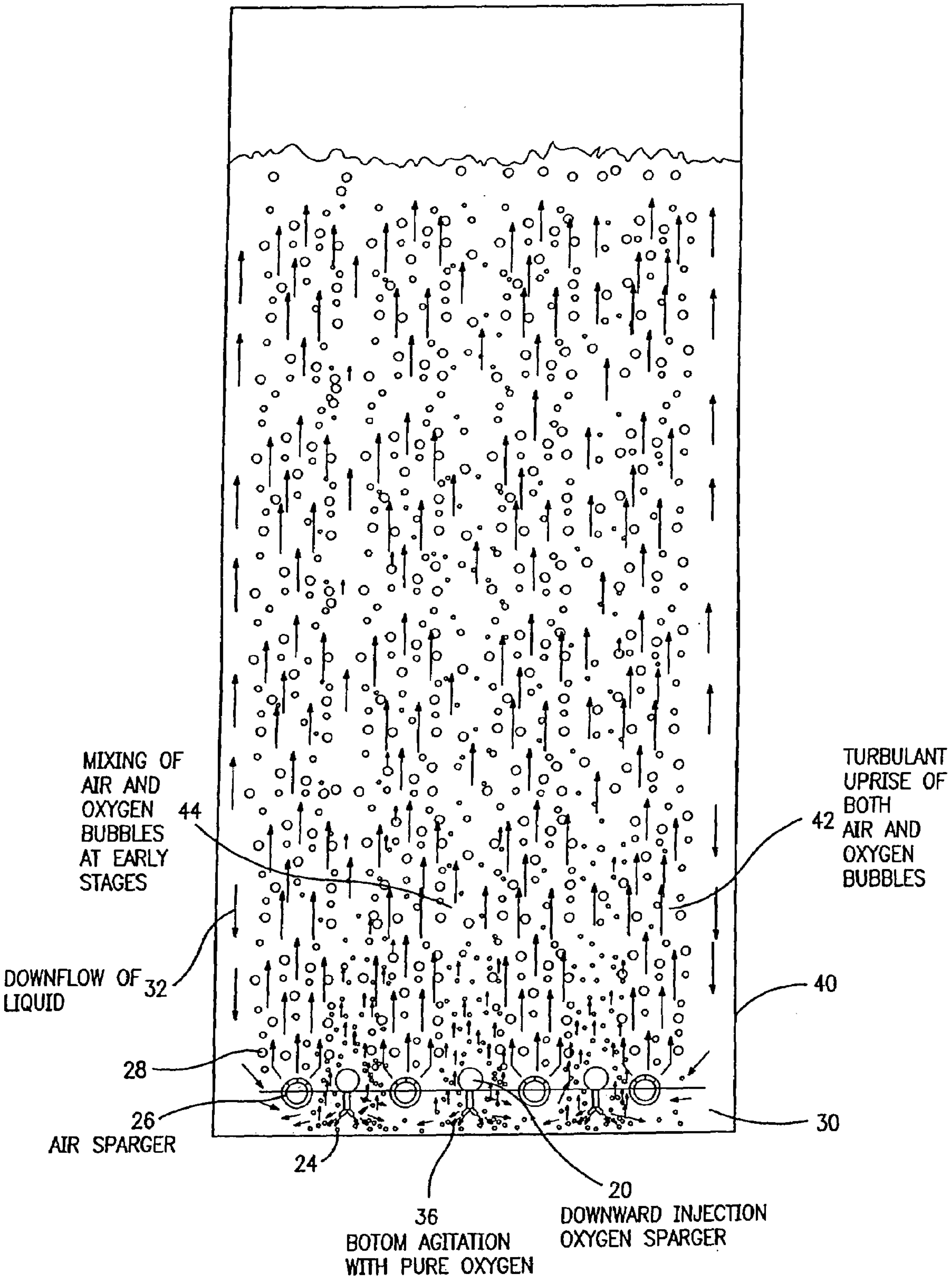
FIG. 3 is a side view of a fermentation vessel showing the alternate positioning of the oxygen spargers and the air spargers therein in this invention.

FIG. 3 shows fermentation vessel 40 having air spargers 26 spaced in between the oxygen spargers 22. Oxygen sparger 22 injects the small oxygen bubbles 24 toward and into the oxygen depleted zone 30 causing bottom agitation 36. The location of the oxygen spargers 22 and the air sparger 26 enables the mixing of the oxygen bubbles 24 and the air bubbles 28 more uniformly throughout the fermentation vessel. Likewise, liquid 32 flows downward on the side of the fermentation vessel 38 towards the edge of the vessel walls and at the bottom proximate to the oxygen depleted zone 30. Oxygen bubbles and air rise upward turbulently 42 throughout vessel 40. Early stages of oxygen bubbles and air take place at the lower portion 44 of the vessel.

Certain alternative embodiments of the spargers are also contemplated in this invention. As mentioned earlier, the sparger pipe does not have to be round. The air-lifted fermenters may be straight pipes forming a grid or any form of arrangement as long as the nozzles are pointing in an angle away from vertical but less than 90% from vertical.

Another alternative to the connect pipe arrangement is to attach the nozzles directly to the sparger. This may complicate fabrication and engineering of the flow restrictor and sparger assembly, but if properly designed, such an embodiment will provide similar benefits.

Another alternative to simple nozzles is the use of flow restrictors 18 in FIG. 1. The flow restrictors can be porous sintered metal plates or calibrated orifices. This allows the nozzles to be fabricated to much larger holes, easier for draining of liquids and cleaning while the flow restrictor provides the actual calibrated flow through each set of nozzles and extension tube. More than two nozzles can be used on the extension tube as a set, as long as the nozzles are clear from the vertical projection of the oxygen spargers.

It should be noted that the foregoing description of the sparger and uses therefor is only illustrative of the invention. Various alternatives and modifications can be devised by those skilled in the art without departing from the invention. Accordingly, the present invention is intended to embrace all such alternatives, modifications and variances that fall within the scope of the appended claims.

What is claimed is:

1. A method for delivering oxygen-containing fluids to a fermentation vessel having an oxygen-depleted zone and comprising both air spargers and oxygen spargers therein, the method comprises injecting air bubbles through the air spargers at the outer end of the vessel, and injecting oxygen bubbles downwardly through the oxygen spargers at the center of the vessel.

2. The method of claim 1, further comprising agitating the oxygen-depleted zone by injecting oxygen bubbles at a downward direction through the oxygen sparger.

3. The method of claim 1, further comprising injecting the oxygen bubbles at a downward direction through the oxygen sparger at an area between the air sparger.

4. The method of claim 1, wherein the oxygen bubbles from the oxygen sparger are smaller than the air bubbles from the air sparger.

5. A method for delivering fluid to a fermentation vessel having an oxygen-depleted zone at the bottom of the vessel and comprising a plurality of air spargers and oxygen spargers therein, with at least one air sparger located next to at least one oxygen sparger, the method comprises injecting air bubbles through the air spargers at one position at the bottom of the vessel, and injecting oxygen bubbles downwardly through the oxygen spargers adjacent to air sparger.

6. The method of claim 5, further comprising agitating the oxygen-depleted zone by injecting oxygen bubbles at a downward direction through the oxygen sparger.

7. The method of claim 5, further comprising injecting the oxygen bubbles at a downward direction through the oxygen sparger at an area between two air spargers.

8. The method of claim 5, wherein the oxygen bubbles from the oxygen sparger are smaller than the air bubbles from the air sparger.

* * * * *